US00RE37950E

(19) United States
(12) Reissued Patent
Dunn et al.

(10) Patent Number: US RE37,950 E
(45) Date of Reissued Patent: *Dec. 31, 2002

(54) BIOGRADABLE IN-SITU FORMING IMPLANTS AND METHODS OF PRODUCING THE SAME

(75) Inventors: Richard L. Dunn, Fort Collins, CO (US); James P. English, Chelsea, AL (US); Donald R. Cowsar, Savannah, GA (US); David P. Vanderbilt, St. Louis, MO (US)

(73) Assignee: Atrix Laboratories, Fort Collins, CO (US)

( * ) Notice: This patent is subject to a terminal disclaimer.

(21) Appl. No.: 09/536,579

(22) Filed: Mar. 28, 2000

Related U.S. Patent Documents

Reissue of:
(64) Patent No.: 5,733,950
Issued: Mar. 31, 1998
Appl. No.: 08/532,540
Filed: Sep. 25, 1995

U.S. Applications:
(60) Continuation of application No. 08/210,891, filed on Mar. 18, 1994, now Pat. No. 5,739,176, which is a continuation of application No. 07/788,032, filed on Dec. 23, 1991, now Pat. No. 5,340,849, which is a division of application No. 07/513,782, filed on Apr. 24, 1990, now Pat. No. 5,278,201, which is a division of application No. 07/252,645, filed on Oct. 3, 1998, now Pat. No. 4,938,763.

(51) Int. Cl.[7] ..... A61K 9/08

(52) U.S. Cl. ..... 523/113; 523/115; 604/49; 604/51; 424/78.38; 424/422; 524/96; 525/413; 525/450

(58) Field of Search ..... 424/78.38, 422; 523/113, 115; 524/96; 525/413, 450; 604/49, 51

(56) References Cited

U.S. PATENT DOCUMENTS

| | | | | |
|---|---|---|---|---|
| 2,155,658 | A | 4/1939 | Hermann et al. | |
| 3,068,188 | A | 12/1962 | Beste et al. | |
| 3,218,283 | A | 11/1965 | Miller et al. | |
| 3,219,527 | A | 11/1965 | Gurney | |
| 3,328,246 | A | 6/1967 | Gottfried, Sr. et al. | |
| 3,463,158 | A | 8/1969 | Schmitt et al. | |
| 3,520,949 | A | 7/1970 | Shepard et al. | 260/857 |
| 3,696,811 | A | 10/1972 | Chen et al. | |
| 3,755,558 | A | 8/1973 | Scribner et al. | |
| 3,760,034 | A | 9/1973 | Critchfield et al. | |
| 3,767,784 | A | 10/1973 | Gluck | 424/28 |
| 3,887,699 | A | 6/1975 | Yolles | |
| 3,931,678 | A | 1/1976 | O'Sullivan et al. | |
| 3,935,308 | A | 1/1976 | Wise et al. | |
| 3,939,111 | A | 2/1976 | Schollenberger et al. | |
| 4,148,871 | A | 4/1979 | Pitt et al. | |
| 4,161,948 | A | 7/1979 | Bichon | |
| 4,408,023 | A | 10/1983 | Gould et al. | |
| 4,439,420 | A | 3/1984 | Mattel et al. | |
| 4,443,430 | A | 4/1984 | Mattel et al. | |
| 4,447,562 | A | 5/1984 | Ivani | |
| 4,450,150 | A | 5/1984 | Sidman | 424/1.1 |
| 4,491,479 | A | 1/1985 | Lauchenauer | |
| 4,568,536 | A | 2/1986 | Kronenthal et al. | |
| 4,570,629 | A | 2/1986 | Widra | |
| 4,582,640 | A | 4/1986 | Smestad et al. | |
| 4,595,713 | A | 6/1986 | St. John | |
| 4,631,188 | A | 12/1986 | Stoy et al. | |
| 4,650,665 | A | 3/1987 | Kronenthal et al. | |
| 4,663,077 | A | 5/1987 | Rei et al. | |
| 4,677,139 | A | 6/1987 | Feinmann et al. | |
| 4,702,917 | A | 10/1987 | Schindler | 424/422 |

(List continued on next page.)

FOREIGN PATENT DOCUMENTS

| | | | |
|---|---|---|---|
| CA | 1261549 | 9/1989 | |
| DE | 2917037 | 4/1980 | |
| EP | 0140766 | 5/1985 | |
| EP | 0169016 | 7/1985 | |
| EP | 0159293 | 10/1985 | |
| EP | 0241178 | 3/1987 | |
| EP | 0244118 | 4/1987 | |
| EP | 0560014 | 1/1993 | |
| EP | 0537559 | 4/1993 | |
| EP | 0539751 | 5/1993 | A61K/9/00 |
| EP | 0649662 | 8/1994 | |
| FR | 21 26270 | 10/1972 | |
| WO | 85/00969 | 3/1985 | |
| WO | 85/02092 | 5/1985 | |

OTHER PUBLICATIONS

*Biocompatibility of Clinical Implant Materisl,* (1976).

*Hawley's Condensed Chemical Dictionary* (*11th Ed.*), Van Nostand Reinhold Co., NY, NY, 224, 555 and 567, (1987).

"Encyclopedia of Polymer Science and Engineering", John Wiley & Sons, Inc., vol. 2, 236–237, (1985).

Billmeyer, *Textbook of Polymer Science, 3rd Ed.*, 390–391, (1984).

Gilding, *Biodegradable Polymers, 9*, 210–232.

Holland, "Polymers–for Biodegradable Medical Devices, 1, The Potential of Polyesters and Controlled Macromolecular Release Systems", *J. of Controlled Release 4*, 155–180, (1986).

*Primary Examiner*—Peter Szekely
(74) *Attorney, Agent, or Firm*—Schwegman, Lundberg, Woessner & Kluth, P.A.

(57) ABSTRACT

A biodegradable polymer is provided for use in providing syringeable, in-situ forming, solid biodegradable implants for animals. The polymer is placed into the animal in liquid form and cures to form the implant in-situ. A thermoplastic system to form said implant comprises the steps of dissolving a non-reactive polymer in biocompatible solvent to form a liquid, placing the liquid within the animal, and allowing the solvent to dissipate to produce the implant. An alternative, thermosetting system comprises mixing together effective amounts of a liquid acrylic ester terminated, biodegradable prepolymer and a curing agent, placing the liquid mixture within an animal and allowing the prepolymer to cure to form the implant. Both systems provide a syringeable, solid biodegradable delivery system by the addition of an effective level of biologically active agent to the liquid before injection into the body.

36 Claims, 2 Drawing Sheets

U.S. PATENT DOCUMENTS 4,715,369 A 12/1987 Suzuki et al.
4,745,160 A 5/1988 Churchill et al.
4,767,627 A 8/1988 Caldwell et al.
4,767,861 A 8/1988 Boulware
4,772,470 A 9/1988 Inoue et al.
4,774,227 A 9/1988 Piez et al.
4,780,320 A 10/1988 Baker
4,793,336 A 12/1988 Wang
4,800,219 A 1/1989 Murdoch et al.
4,804,691 A 2/1989 English et al. ..... 523/118
4,920,203 A 4/1990 Tang ..... 523/105
4,938,763 A 7/1990 Dunn et al. ..... 604/891.1
4,981,696 A 1/1991 Loomis ..... 424/426
4,983,689 A 1/1991 Yu ..... 525/415
5,013,553 A 5/1991 Southard ..... 424/58
5,077,049 A 12/1991 Dunn et al. ..... 424/426
5,278,201 A 1/1994 Dunn et al. ..... 523/113
5,278,202 A 1/1994 Dunn et al. ..... 523/113
5,286,763 A 2/1994 Gerhart ..... 514/772.4
5,324,519 A 6/1994 Dunn et al. ..... 424/426
5,324,520 A 6/1994 Dunn et al. ..... 424/435
5,340,849 A 8/1994 Dunn et al. ..... 523/113
5,368,859 A 11/1994 Dunn et al. ..... 434/426
4,938,763 A 7/1995 Dunn et al. ..... 424/422

BIOGRADABLE IN-SITU FORMING IMPLANTS AND METHODS OF PRODUCING THE SAME

Matter enclosed in heavy brackets [ ] appears in the original patent but forms no part of this reissue specification; matter printed in italics indicates the additions made by reissue.

CROSS-REFERENCE TO RELATED APPLICATIONS

This application is a continuation of U.S. patent application Ser. No. 08/210,891, filed Mar. 18, 1994, *now U.S. Pat. No. 5,739,176 (issued Apr. 14, 1998),* which is a continuation of U.S. patent application Ser. No. 07/788,032, filed Dec. 23, 1991, now U.S. Pat. No. 5,340,849 (issued Aug. 23, 1994), which is a division of U.S. patent application Ser. No. 07/513,782, filed Apr. 24, 1990, now U.S. Pat. No. 5,278, 201 (issued Jan. 11, 1994), which is a division of U.S. patent application Ser. No. 07/252,645, filed Oct. 3, 1988, now U.S. Pat. No. B1-4,938,763 (issued Jul. 3, 1990; certificate issued Jul. 4, 1995).

BACKGROUND OF THE INVENTION

The present invention relates to a method and composition for producing biodegradable polymers, and more particularly to the use of such polymers for providing syringeable, in-situ forming, solid, biodegradable implants.

Biodegradable polymers have been used for many years in medical applications. These include sutures, surgical clips, staples, implants, and drug delivery systems. The majority of these biodegradable polymers have been thermoplastic materials based upon glycolide, lactide, ϵ-caprolactone, and copolymers thereof. Typical examples are the polyglycolide sutures described in U.S.-Pat. No. 3,297,033 to Schmitt, the poly(L-lactide-co-glycolide) sutures described in U.S. Pat. No. 3,636,956 to Schneider, the poly(L-lactide-co-glycolide) surgical clips and staples described in U.S. Pat. No. 4,523,591 to Kaplan et al., and the drug-delivery systems described in U.S. Pat. No. 3,773,919 to Boswell et al., U.S. Pat. No. 3,887,699 to Yolles, U.S. Pat. No. 4,155,992 to Schmitt, U.S. Pat. No. 4,379,138 to Pitt et al., and U.S. Pat. Nos. 4,130,639 and 4,186,189 to Shalaby et al.

All of the biodegradable polymers described in these patents are thermoplastic materials. Consequently, they can be heated and formed into various shapes such as fibers, clips, staples, pins, films, etc. Only when heated above their melting point do these polymers become liquid. During their normal use, they are solids.

Thermoset biodegradable polymers have also been previously described for use in medical applications. These polymers have been formed by crosslinking reactions which lead to high-molecular-weight materials that do not melt or form flowable liquids at high temperatures. Typical examples of these materials are the crosslinked polyurethanes described in U.S. Pat. No. 2,933,477 to Hostettler and U.S. Pat. No. 3,186,971 to Hostettler et al. Copolymers based on ϵ-caprolactone and L-lactide or DL-lactide crosslinked via peroxide initiators were described in U.S. Pat. Nos. 4,045,418 and 4,057,537, both to Sinclair. Crosslinked caprolactone copolymers have been prepared by incorporation of a bislactone into a monomer feed, as described in U.S. Pat. No. 4,379,138 to Pitt et al. Trihydroxy-functional copolymers of ϵ-caprolactone and ϵ-valerolactone have been crosslinked with diisocyanates, thereby affording biodegradable polymers, as described in Pitt et al., J. Polym. Sci.: Part A: Polym Chem. 25:955–966; 1987. These polymers are also solids when crosslinked or cured.

Although these two classes of biodegradable polymers have many useful biomedical applications, there are several important limitations to their use in the body where body is defined as that of humans, animals, birds, fish, and reptiles. Because these polymers are solids, all instances involving their use have required initially forming the polymeric structures outside the body, followed by insertion of the solid structure into the body. For example, sutures, clips, and staples are all formed from thermoplastic biodegradable polymers prior to use. When inserted into the body, they retain their original shape rather than flow to fill voids or cavities where they may be most needed.

Similarly, drug-delivery systems using these biodegradable polymers have to be formed outside the body. In such instances, the drug is incorporated into the polymer and the mixture shaped into a certain form such a cylinder, disc, or fiber for implantation. With such solid implants, the drug-delivery system has to be inserted into the body through an incision. These incisions are often larger than desired by the medical profession and lead to a reluctance of the patients to accept such an implant or drug-delivery system.

The only way to avoid the incision with these polymers is to inject them as small particles, microspheres, or microcapsules. These may or may not contain a drug which can be released into the body. Although these small particles can be injected into the body with a syringe, they do not always satisfy the demand for a biodegradable implant. Because they are particles, they do not form a continuous film or solid implant with the structural integrity needed for certain prostheses. When inserted into certain body cavities such as the mouth, a periodontal pocket, the eye, or the vagina where there is considerable fluid flow, these small particles, microspheres, or microcapsules are poorly retained because of their small size and discontinuous nature. In addition, microspheres or microcapsules prepared from these polymers and containing drugs for release into the body are sometimes difficult to produce on a large scale, and their storage and injection characteristics present problems. Furthermore, one other major limitation of the microcapsule or small-particle system is their lack of reversibility without extensive surgical intervention. That is, if there are complications after they have been injected, it is considerably more difficult to remove them from the body than with solid implants.

Therefore, there exists a need for a method and composition which provides a biodegradable, polymeric structure useful in overcoming the above-described limitations.

There exists a further need for a method and composition for providing syringeable, in-situ forming, solid, biodegradable implants which can be used as prosthetic devices and/or controlled delivery systems.

Moreover, there exists a need for such a method and composition which can provide implants having a range of properties from soft to rigid, so as to be usable with both soft and hard tissue.

SUMMARY OF THE PRESENT INVENTION

The present invention relates to the production and use of biodegradable polymers as prosthetic implants and controlled-release, drug-delivery systems which can be administered as liquids via, for example, a syringe and needle, but which coagulate or cure ("set") shortly after dosing to form a solid. The implants are biodegradable because they are made from biodegradable polymers and copolymers comprising two types of polymer systems: thermoplastic and thermosetting.

A thermoplastic system is provided in which a solid, linear-chain, biodegradable polymer or copolymer is dissolved in a solvent, which is nontoxic and water miscible, to form a liquid solution. Once the polymer solution is placed into the body where there is sufficient water, the solvent dissipates or diffuses away from the polymer, leaving the polymer to coagulate or solidify into a solid structure. The placement of the solution can be anywhere within the body, including soft tissue such as muscle or fat, hard tissue such as bone, or a cavity such as the periodontal, oral, vaginal, rectal, nasal, or a pocket such as a periodontal pocket or the cul-de-sac of the eye. For drug-delivery systems, the biologically active agent is added to the polymer solution where it is either dissolved to form a homogeneous solution or dispersed to form a suspension or a dispersion of drug within the polymeric solution. When the polymer solution is exposed to body fluids or water, the solvent diffuses away from the polymer-drug mixture and water diffuses into the mixture where it coagulates the polymer thereby trapping or encapsulating the drug within the polymeric matrix as the implant solidifies. The release of the drug then follows the general rules for diffusion or dissolution of a drug from within a polymeric matrix.

Another embodiment of the invention is also provided, namely, a thermosetting system comprising the synthesis of crosslinkable polymers which are biodegradable and which can be formed and cured in-situ. The thermosetting system comprises reactive, liquid, oligomeric polymers which contain no solvents and which cure in place to form solids, usually with the addition of a curing catalyst.

The multifunctional polymers useful in the thermosetting system are first synthesized via copolymerization of either DL-lactide of L-lactide with ϵ-caprolactone using a multifunctional polyol initiator and a catalyst to form polyol-terminated prepolymers. The polyol-terminated prepolymers are then converted to acrylic ester-terminated prepolymers, preferably by acylation of the alcohol terminus with acryloyl chloride via a Schotten-Baumann-like technique, i.e., reaction of acyl halides with alcohols. The acrylic ester-terminated prepolymers may also be synthesized in a number of other ways, including but not limited to, reaction of carboxylic acids (i.e., acrylic or methacrylic acid) with alcohols, reaction of carboxylic acid esters (i.e., methyl acrylate or methyl methacrylate) with alcohols by transesterification, and reaction of isocyanatoalkyl acrylates (i.e., isocyanatoethyl methacrylate) with alcohols.

The liquid acrylic-terminated prepolymer is cured, preferably by the addition of benzoyl peroxide or azobisisobutyronitrile, to a more solid structure. Thus, for an implant utilizing these crosslinkable polymers, the catalyst is added to the liquid acrylic-terminated prepolymer immediately prior to injection into the body. Once inside the body, the crosslinking reaction will proceed until sufficient molecular weight has been obtained to cause the polymer to solidify. The liquid prepolymer, when injected, will flow into the cavity or space in which it is placed and assume that shape when it solidifies. For drug delivery utilizing this system, biologically active agents are added to the liquid polymer systems in the uncatalyzed state.

In both the thermoplastic and the thermosetting systems, the advantages of liquid application are achieved. For example, the polymer may be injected via syringe and needle into a body while it is in liquid form and then left in-situ to form a solid biodegradable implant structure. The need to form an incision is eliminated, and the implant will assume the shape of its cavity. Furthermore, a drug-delivery vehicle may be provided by adding a biologically active agent to the liquid prior to injection. Once the implant is formed, it will release the agent to the body and then biodegrade. The term "biologically active agent" means a drug or some other substance capable of producing an effect on a body.

It is an object of the present invention, therefore, to provide a method and composition for producing biodegradable polymers.

It is also an object of the present invention to provide such a polymer which may be useful in producing syringeable, in-situ forming, solid biodegradable implants.

It is a further object of the present invention to provide such an implant which can be used in a controlled-release delivery system for biological agents.

It is a further object of the present invention to provide implants having a range of properties from soft and elastomeric to hard and rigid, so as to be usable with both soft and hard tissue.

BRIEF DESCRIPTION OF THE FIGURES AND TABLES

Figure 1:
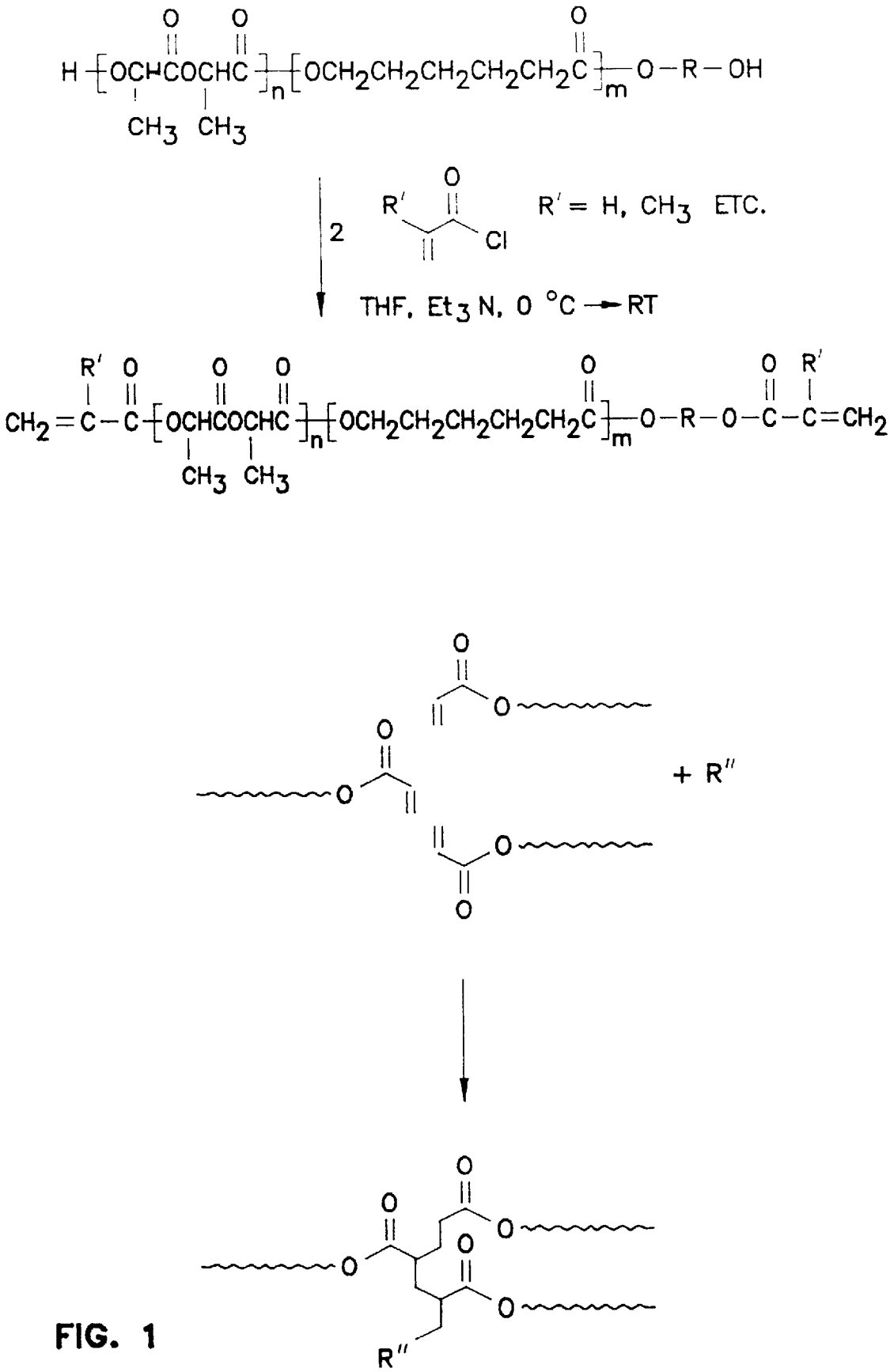
FIG. 1 illustrates the synthesis of acrylate-terminated prepolymers and subsequent crosslinking by free-radical initiators.

Table 1 is a summary of the bifunctional PLC prepolymers synthesized;

Table 2 is a summary of the acrylic ester terminated prepolymers synthesized; and Table 3 is a summary of curing studies.

DETAILED DESCRIPTION OF THE INVENTION

The present invention relates to biodegradable, in-situ forming implants and methods for producing the same. The present invention also relates to a liquid biodegradable polymeric delivery system that can be injected into a body where it forms a solid and releases a biologically active agent at a controlled rate. Two types of biodegradable polymeric systems are described: thermoplastic copolymers dissolved in a biocompatible solvent and thermosetting polymers that are liquids without the use of solvents.

A. Thermoplastic System

A thermoplastic system is provided in which a solid, linear-chain, biodegradable polymer is dissolved in a biocompatible solvent to form a liquid, which can then be administered via a syringe and needle. Examples of biodegradable polymers which can be used in this application are polylactides, polyglycolides, polycaprolactones, polyanhydrides, polyamides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly (amino acids), polyvinylpyrrolidone, polyethylene glycol, polyhydroxycellulose, chitin, chitosan, and copolymers, terpolymers, or combinations or mixtures of the above materials. The preferred polymers are those which have a lower degree of crystallization and are more hydrophobic. These polymers and copolymers are more soluble in the biocompatible solvents than the highly crystalline polymers such as polyglycolide and chitin which also have a high degree of hydrogen-bonding. Preferred materials with the desired solubility parameters are the polylactides, polycaprolactones, and copolymers of these with glycolide in which there are more amorphous regions to enhance solubility.

It is also preferred that the solvent for the biodegradable polymer be non-toxic, water miscible, and otherwise biocompatible. Solvents that are toxic should not be used to inject any material into a living body. The solvents must also be biocompatible so that they do not cause severe tissue irritation or necrosis at the site of implantation. Furthermore, the solvent should be water miscible so that it will diffuse quickly into the body fluids and allow water to permeate into the polymer solution and cause it to coagulate or solidify. Examples of such solvents include N-methyl-2-pyrrolidone, 2-pyrrolidone, ethanol, propylene glycol, acetone, methyl acetate, ethyl acetate, methyl ethyl ketone, dimethylformamide, dimethyl sulfoxide, tetrahydrofuran, caprolactam, decylmethylsulfoxide, oleic acid, and 1-dodecylazacycloheptan-2-one. The preferred solvents are N-methyl-2-pyrrolidone, 2-pyrrolidone, dimethyl sulfoxide, and acetone because of their [solrating] *solvating* ability and their compatibility.

The solubility of the biodegradable polymers in the various solvents will differ depending upon their crystallinity, their hydrophilicity, hydrogen-bonding, and molecular weight. Thus, not all of the biodegradable polymers will be soluble in the same solvent, but each polymer or copolymer should have its optimum solvent. Lower molecular-weight polymers will normally dissolve more readily in the solvents than high-molecular-weight polymers. As a result, the concentration of a polymer dissolved in the various solvents will differ depending upon type of polymer and its molecular weight. Conversely, the higher molecular-weight polymers will normally tend to coagulate or solidify faster than the very low-molecular-weight polymers. Moreover the higher molecular-weight polymers will tend to give higher solution viscosities than the low-molecular-weight materials. Thus for optimum injection efficiency, the molecular weight and the concentration of the polymer in the solvent have to be controlled.

For example, low-molecular-weight polylactic acid formed by the condensation of lactic acid will dissolve in N-methyl-2-pyrrolidone(NMP) to give a 73% by weight solution which still flows easily through a 23-gauge syringe needle, whereas a higher molecular-weight poly(DL-lactide) (DL-PLA) formed by the additional polymerization of DL-lactide gives the same solution viscosity when dissolved in NMP at only 50% by weight. The higher molecular-weight polymer solution coagulates immediately when placed into water. The low-molecular-weight polymer solution, although more concentrated, tends to coagulate very slowly when placed into water.

For polymers that tend to coagulate slowly, a solvent mixture can be used to increase the coagulation rate. Thus one liquid component of the mixture is a good solvent for the polymer, and the other component is a poorer solvent or a non-solvent. The two liquids are mixed at a ratio such that the polymer is still soluble but precipitates with the slightest increase in the amount of non-solvent, such as water in a physiological environment. By necessity, the solvent system must be miscible with both the polymer and water. An example of such a binary solvent system is the use of NMP and ethanol for low-molecular-weight DL-PLA. The addition of ethanol to the NMP/polymer solution increases its coagulation rate significantly.

It has also been found that solutions containing very high concentrations of high-molecular-weight polymers sometimes coagulate or solidify slower than more dilute solutions. It is suspected that the high concentration of polymer impedes the diffusion of solvent from within the polymer matrix and consequently prevents the permeation of water into the matrix where it can precipitate the polymer chains. Thus, there is an optimum concentration at which the solvent can diffuse out of the polymer solution and water penetrates within to coagulate the polymer.

In one envisioned use of the thermoplastic system, the polymer solution is placed in a syringe and injected through a needle into the body. Once in place, the solvent dissipates, the remaining polymer solidifies, and a solid structure is formed. The implant will adhere to its surrounding tissue or bone by mechanical forces and can assume the shape of its surrounding cavity. Thus, the biodegradable polymer solution can be injected subdermally like collagen to build up tissue or to fill in defects. It can also be injected into wounds including burn wounds to prevent the formation Of deep scars. Unlike collagen, the degradation time of the implant can be varied from a few weeks to years depending upon the polymer selected and its molecular weight. The injectable polymer solution can also be used to mend bone defects or to provide a continuous matrix when other solid biodegradable implants such as hydroxyapatite plugs are inserted into bone gaps. The injectable system can also be used to adhere tissue to tissue or other implants to tissue by virtue of its mechanical bonding or encapsulation of tissue and prosthetic devices.

Another envisioned use of the thermoplastic system is to provide a drug-delivery system. In this use, a bioactive agent is added to the polymer solution prior to injection, and then the polymer/solvent/agent mixture is injected into the body. In some cases, the drug will also be soluble in the solvent, and a homogeneous solution of polymer and drug will be available for injection. In other cases, the drug will not be soluble in the solvent, and a suspension or dispersion of the drug in the polymer solution will result. This suspension or dispersion can also be injected into the body. In either case, the solvent will dissipate and the polymer will solidify and entrap or encase the drug within the solid matrix. The release of drug from these solid implants will follow the same general rules for release of a drug from a monolithic polymeric device. The release of drug can be affected by the size and shape of the implant, the loading of drug within the implant, the permeability factors involving the drug and the particular polymer, and the degradation of the polymer. Depending upon the bioactive agent selected for delivery, the above parameters can be adjusted by one skilled in the art of drug delivery to give the desired rate and duration of release.

The term drug or bioactive (biologically active) agent as used herein includes without limitation physiologically or pharmacologically active substances that act locally or systemically in the body. Representative drugs and biologically active agents to be used with the syringeable, in-situ forming solid implant systems include, without limitation, peptide drugs, protein drugs, desensitizing agents, antigens, vaccines, anti-infectives, antibiotics, antimicrobials, antiallergenics, steroidal anti-inflammatory agents, antiallergenics, steroidal anti-inflammatory agents, decongestants, miotics, anticholinergios, sympathomimetics, sedatives, hypnotics, psychic energizers, tranquilizers, androgenic steroids, estrogens, progestational agents, humoral agents, prostaglandins, analgesics, antispasmodics, antimalarials, antihistamines, cardioactive agents, non-steroidal anti-inflammatory agents, antiparkinsonian agents, antihypertensive agents, β-adrenergic blocking agents, nutritional agents, and the benzophenanthridine alkaloids. To those skilled in the art, other drugs or biologically active agents that can be released in an aqueous environment can be utilized in the described injectable delivery system. Also, various forms of the drugs or biologically active agents may be used. These include without limitation forms such as uncharged molecules, molecular complexes, salts, ethers, esters, amides, etc., which are biologically activated when injected into the body.

The amount of drug or biologically active agent incorporated into the injectable, in-situ, solid forming implant depends upon the desired release profile, the concentration of drug required for a biological effect, and the length of time that the drug has to be released for treatment. There is no critical upper limit on the amount of drug incorporated into the polymer solution except for that of an acceptable solution or dispersion viscosity for injection through a syringe needle. The lower limit of drug incorporated into the delivery system is dependent simply upon the activity of the drug and the length of time needed for treatment.

In all cases, the solid implant formed within the injectable polymer solution will slowly biodegrade within the body and allow natural tissue to grow and replace the impact as it disappears. Thus, when the material is injected into a soft-tissue defect, it will fill that defect and provide a scaffold for natural collagen tissue to grow. This collagen tissue will gradually replace the biodegradable polymer. With hard tissue such as bone, the biodegradable polymer will support the growth of new bone cells which will also gradually replace the degrading polymer. For drug-delivery systems, the solid implant formed from the injectable system will release the drug contained within its matrix at a controlled rate until the drug is depleted. With certain drugs, the polymer will degrade after the drug has been completely released. With other drugs such as peptides or proteins, the drug will be completely released only after the polymer has degraded to a point where the non-diffusing drug has been exposed to the body fluids.

B. Thermosetting System

The injectable, in-situ forming biodegradable implants can also be produced by crosslinking appropriately functionalized biodegradable polymers. The thermosetting system comprises reactive, liquid, oligomeric polymers which cure in place to form solids, usually with the addition of a curing catalyst. Although any of the biodegradable polymers previously described for the thermoplastic system can be used, the limiting criteria is that low-molecular-weight oligomers of these polymers or copolymers must be liquids and they must have functional groups on the ends of the prepolymer which can be reacted with acryloyl chloride to produce acrylic ester capped prepolymers.

The preferred biodegradable system is that produced from poly(DL-lactide-co-caprolactone), or "DL-PLC". Low-molecular-weight polymers or oligomers produced from these materials are flowable liquids at room temperature. Hydroxy-terminated PLC prepolymers may be synthesized via copolymerization of DL-lactide or L-lactide and ε-caprolactone with a multifunctional polyol initiator and a catalyst. Catalysts useful for the preparation of these prepolymers are preferably basic or neutral ester-interchange (transesterification) catalysts. Metallic esters of carboxylic acids containing up to 18 carbon atoms such as formic, acetic, lauric, stearic, and benzoic are normally used as such catalysts. Stannous octoate and stannous chloride are the preferred catalysts, both for reasons of FDA compliance and performance.

If a bifunctional polyester is desired, a bifunctional chain initiator such as ethylene glycol is employed. A trifunctional initiator such as trimethylolpropane produces a trifunctional polymer, etc. The amount of chain initiator used determines the resultant molecular weight of the polymer or copolymer. At high concentration of chain initiator, the assumption is made that one bifunctional initiator molecule initiates only one polymer chain. On the other hand, when the concentration of bifunctional initiator is very low, each initiator molecule can initiate two polymer chains. In any case, the polymer chains are terminated by hydroxyl groups, as seen in FIG. 1. In this example, the assumption has been made that only one polymer chain is initiated per bifunctional initiator molecule. This assumption allows the calculation of a theoretical molecular weight for the prepolymers.

A list of the bifunctional PLC prepolymers that were synthesized is given in Table 1. Appropriate amounts of DL-lactide, ε-caprolactone, and ethylene glycol were combined in a flask under nitrogen and then heated in an oil bath at 155° C. to melt and mix the monomers. The copolymerizations were then catalyzed by the addition of 0.03 to 0.05 wt % $SnCl_2$. The reaction was allowed to proceed overnight. The hydroxyl numbers of the prepolymers were determined by standard titration procedure. The Gardner-Holdt viscosities of the liquid prepolymers Were also determined using the procedures outlined in ASTM D 1545. The highest molecular-weight prepolymer (MW=5000) was a solid at room temperature; therefore, its Gardner-Holdt viscosity could not be determined.

Figure 2:
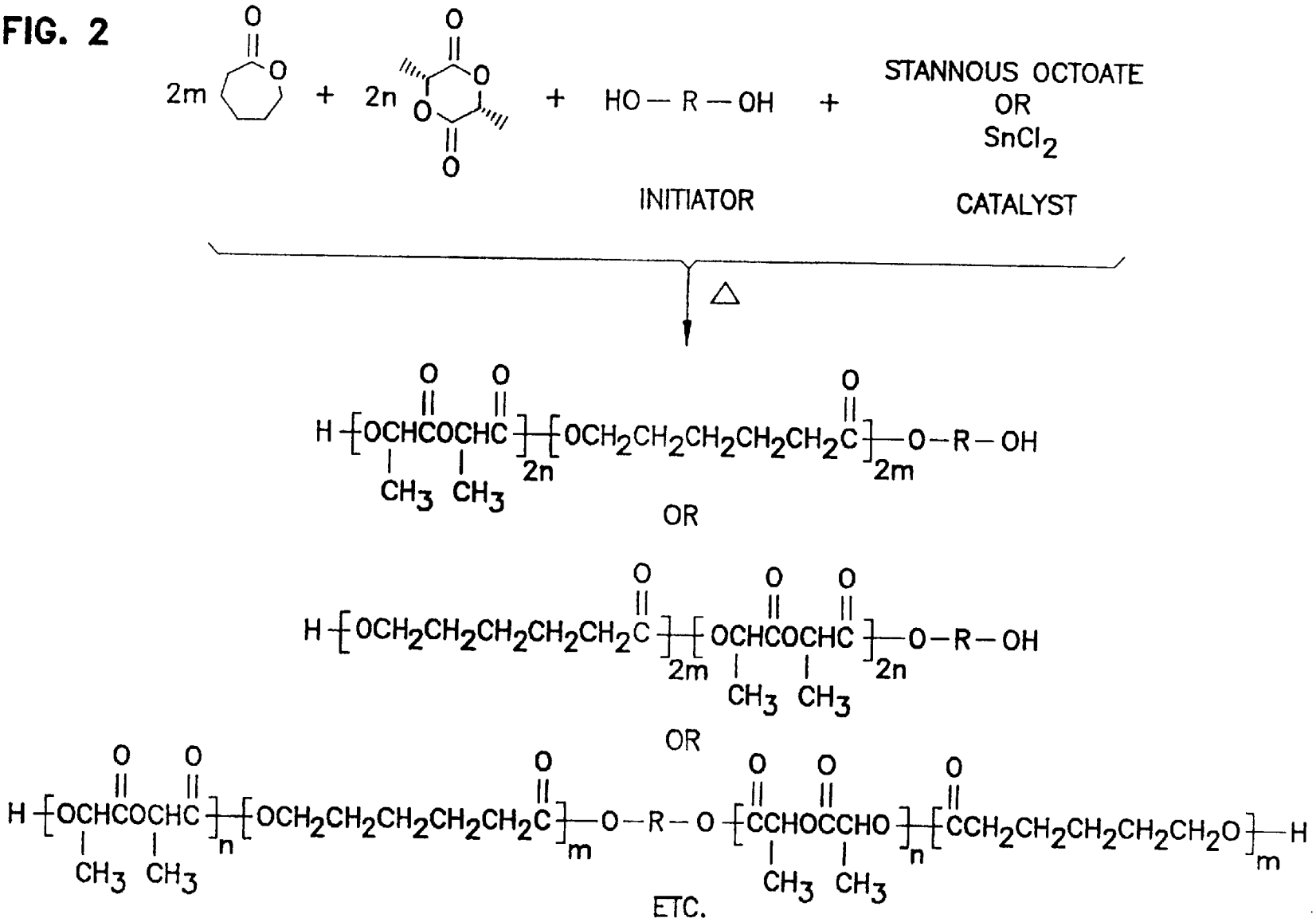
FIG. 2 illustrates structures for the random copolymer of ϵ-caprolactone and L-lactide initiated with a diol.

The diol prepolymers were converted to acrylic-ester-capped prepolymers via a reaction with acryloyl chloride under Schotten-Baumann-like conditions, as seen in FIG. 2 and summarized in Table 2. Other methods of converting the diol prepolymers to acrylic-ester-capped prepolymers may also be employed.

Both THF and dichloromethane were evaluated as solvents in the acylation reactions. Several problems were encountered when THF was used as the solvent. The triethylamine hydrochloride formed as a by-product in the reaction was so finely divided that it could not be efficiently removed from the reaction mixture by filtration. Triethylamine hydrochloride ($Et_3N$-HCl) has been reported to cause polymerization of acrylic species (U.S. Pat. No. 4,405,798). In several instances, where attempts to remove all of the $Et_3N$.HCl failed, the acrylic-ester-capped prepolymers gelled prematurely. Thus, to effectively remove all of the $Et_3N$.HCl, it was necessary to extract the prepolymers with water. For reactions carried out in THF, it is preferred that one first evaporate the THF in vacuo, redissolve the oil in $CH_2Cl_2$, filter out the $Et_3N$-HCl, and then extract the $CH_2Cl_2$ layer with water. Stable emulsions were sometimes encountered during extraction. The acylations were later carried out in $CH_2Cl_2$ instead of THF. The filtration of $Et_3N$.HCl from the reaction mixture was found to be much easier using this solvent, and the organic fraction could be extracted directly with water after filtration.

Both diol and acrylic prepolymers were examined by IR and $^1H$ NMR spectroscopy. The salient feature of the IR spectra of diol prepolymers is a prominent O—H stretch centered at approximately 3510 $cm^{-1}$. Upon acylation, the intensity of the O—H stretch decreases markedly, and new absorbances at approximately 1640 $cm^{-1}$ appear. These new absorbances are attributed to the C—C stretch associated with acrylic groups. Likewise, the presences of acrylic ester groups is apparent in the $^1H$ NMR spectra, the characteristic resonances for the vinyl protons falling in the range of 5.9 to 6.6 ppm.

The acrylic prepolymers and diol prepolymers were then cured, as summarized in Table 3. The general procedure for the curing of the prepolymers is now described: to 5.0 g of acrylic prepolymer contained in a small beaker was added a solution of benzoyl peroxide (BP) in approximately 1 mL of $CH_2Cl_2$. In some cases, fillers or additional acrylic monomers were added to the prepolymers prior to the introduction of the BP solution. The mixtures were stirred thoroughly and then poured into small petri dishes. The dishes were placed in a preheated vacuum oven for curing. Some of the samples were cured in air and not in vacuo, and these samples are so indicated in Table 3.

This thermosetting system may be used wherever a biodegradable implant is desired. For example, because the prepolymer remains a liquid for a short time after addition of the curing agent, the liquid prepolymer/curing agent mixture may be placed into a sytringe and injected into a body. The mxiture than solidifies in-situ, thereby providing an implant without an incision. Furthermore, a drug-delivery system may be provided by adding a biologically active agent to the prepolymer prior to injection. Once in-situ, the system will cure to a solid; eventually, it will biodegrade, and the agent will be gradually released.

DETAILED DESCRIPTION OF EXAMPLES

The following examples are set forth as representative of the present invention. These examples are not to be construed as limiting the scope of the invention as these and other equivalent embodiments will be apparent in view of the present disclosure, figures, and accompanying claims.

EXAMPLE 1

Poly(DL-lactic acid) was prepared by the simple polycondensation of lactic acid. No catalysts were used, and the reaction times were varied to produce polymers with different theoretical molecular weights. These polymers were designated as DL-PLA oligomers. A quantity of the solid oligomer was dissolved in NMP to give a 68:32 ratio of polymer to solvent. Sanguinarine chloride(SaCl), a benzophenanthridine alkaloid with antimicrobial activity especially toward periodontal pathogens, was added to the polymer solution to give a 2% by weight dispersion of the drug in the total mixture. The dispersion of drug and polymer solution was then injected into a dialysis tube (diameter of 1.5 mm) with a sterile disposable syringe without a needle. Each end of the 6-in. length of dialysis tubing was tied with a knot to prevent loss of the drug/polymer mass, and the tube with the injected material was placed in a pH 7 Sorenson's buffer receiving fluid maintained at 37° C. Upon immersion in the receiving fluid, the drug/polymer mass coagulated into a solid mass, and the drug began to be released from the polymer as indicated by an orange-red color in the receiving fluid. The quantity of solution injected into the dialysis tube was about 250 $\mu$L or about 100 mg of solids.

The dialysis tubing was selected to have a molecular-weight cutoff of about 3,500. With this molecular-weight cutoff, the SaCl released from the polymer could easily diffuse through the walls of the tubing, but any solid polymer would be retained. The dialysis tubing containing the drug/polymer matrix was removed frequently and placed in a bottle of fresh receiving fluid. The old receiving fluid containing the released drug was then acidified to a pH of 2.76 to convert all released drug to the iminium ion form of the drug, and the concentration of drug was determined by measuring the ultraviolet absorption (UV) at a wavelength of 237 nm. The cumulative mass of drug released and the cumulative fraction were then calculated and plotted as a function of time. Approximately 60% of the drug was released in the first day, 72% after 2 days, 85% after 5 days, 90% after 9 days, and 97% after 14 days.

EXAMPLE 2

Ethoxydihydrosanguinarine(SaEt), the ethanol ester of sanguinarine, was added to the same DL-PLA oligomer/NMP solution described in Example 1. SaEt dissolved in the polymer solution to give a homogeneous solution of drug and polymer. Approximately 250 $\mu$L of the solution was added to receiving fluid and the release of drug measured as described in Example 1. The release of SaEt was slower than that for SaCl as expected because of its lower water solubility. After the first day, approximately 45% was released, 52% after 2 days, 60% after 5 days, 70% after 9 days, and 80% after 14 days.

EXAMPLE 3

Poly(DL-lactide) with an inherent viscosity of 0.08 dL/g and a theoretical molecular weight of 2,000 was prepared by the ring-opening polymerization of DL-lactide using lauryl alcohol as the initiator and stannous chloride as the catalyst. This polymer was then dissolved in NMP to give a 40% by weight polymer solution. SaCl was dispersed in the solution of this polymer in NMP to give a 1.5% by weight dispersion of the drug in the solution and the release rate determined as described in Example 1. The release rate of the drug from this higher molecular-weight polymer was slower than from the DL-PLA oligomer. After the first day, approximately 32% was released, 40% after 2 days, 45% after 5 days, and 50% after 15 days.

EXAMPLE 4

SaEt was added to the same polymer solution of DL-PLA in NMP as described in Example 3. A homogeneous solution with the drug at 1.5% by weight was obtained. The release of drug from this solution determined using the same procedure described in Example 1 gave a much slower release of SaEt than from the DL-PLA oligomer. After the first day approximately 8% was released, 14% after 2 days, 20% after 5 days, 23% after 9 days, and 28% after 14 days.

EXAMPLE 5

The effect of drug loading on the release of drug from the polymer solutions were demonstrated by adding SaCl to a 40% by weight of DL-PLA oligomer in NMP. The drug was dispersed in the polymer solution to give 2, 7 and 14% by weight dispersions. The release of drug from these formulations using the same procedure as described in Example 1 showed that the higher drug loading gave a lower fractional rate of release as normally obtained for matrix delivery systems with diffusional release. The 2% -loaded formulation gave 65% release after 1 day, 75% after 2 days, and 88% after 5 days; the 7%-loaded formulation gave 48% release after 1 day, 52% after 2 days, and 58% after 5 days; and the 14%-loaded formulation gave 38% release after 1 day, 43% after 2 days, and 49% after 5days.

EXAMPLE 6

Poly(DL-lactide-co-glycolide) was prepared by the ring-opening polymerization of a mixture of DL-lactide and glycolide using lauryl alcohol as the initiator and stannous chloride as the catalyst. The proportions of the two monomers were adjusted so that the final copolymer(DL-PLG) had a 50:50 ratio of the two monomers as determined by nuclear magnetic resonance spectrophotometry. The initiator was also adjusted to give a copolymer with a theoretical molecular weight of 1500 daltons. The copolymer was dissolved in NMP to give a 70% by weight polymer solution. SaCl was added to this solution to give a 2% by weight dispersion of the drug in the polymer solution. The release of drug from this formulation was determined using the same procedure described in Example 1. A much lower release rate was obtained from the copolymer than from the DL-PLA oligomer of DL-PLA 2000 molecular weight materials. After 2 days approximately 7% of the drug was released, 10% after 5 days, 12% after 7 days, and 16% after 14 days.

EXAMPLE 7

SaEt was added to the same solution of DL-PLG in NMP as described in Example 6 to give a 2% by weight solution of the drug. The release of drug from this formulation was determined by the same procedure as described previously. The release rate of SaEt from this formulation was identical to that for SaCl described in Example 6.

EXAMPLE 8

Tetracycline as the free base (TCB) was added to the same solution of DL-PLG in NMP as described in Example 6. The drug dissolved completely in the polymer solution to give a 2.4% by weight solution to the drug. The release of the drug from this formulation was determined by a similar procedure to that described in Example 1 except the receiving fluid was not acidified to a pH of 2.76 and the concentration of TCB was determined by UV absorption at the wavelength appropriate for the drug. The release of TCB from this formulation was more linear and at a much higher rate than that for SaCl or SaEt from the same copolymer. After 1 day approximately 44% of the drug was released, 54% after 2 days, 68% after 5 days, 73% after 6 days, 80% after 7 days, 87% after 9 days, 96% after 12 days, and 100% after 14 days.

EXAMPLE 9

Tetracycline as the hydrochloride salt (TCH) was added to the same solution of DL-PLG in NMP as described in Example 6. The salt form of the drug also dissolved completely in the polymer solution. The release of drug from this formulation was determined as described in Example 8 and found to be similar to that for the free base except for a slightly lower rate. After 1 day approximately 32% of the drug was released, 40% after 2 days, 57% after 5 days, 64% after 6 days, 75% after 7 days, 82% after 9 days, 92% after 12 days, and 100% after 14 days.

EXAMPLE 10

DL-PLA with an inherent viscosity of 0.26 dL/g and a theoretical molecular weight of approximately 10,000 daltons was prepared by the ring-opening polymerization of DL-lactide using lauryl alcohol as the initiator and stannous chloride at the catalyst. The polymer was dissolved in NMP to give a 50% by weight polymer solution. A quantity of the polymer solution (100 $\mu$L) was injected subdermally into rabbits, and the tissue reaction was compared to that of a USP negative plastic. The test sites were evaluated for signs of local irritation, in accordance with the Draize method, immediately after injection, at 1 and 6 hours post injection, and once daily thereafter until scheduled sacrifice at 7, 14 or 21 days. The reaction at the test sites was equivalent to that at the control USP negative plastic. The polymer solution (100 $\mu$L) was also administered subgingivally into sites created by dental extractions in Beagle dogs. Control sites were flushed with saline solution. The dogs were examined daily for signs of mortality, pharmacotoxic effects, body weights, and local gingival irritation. The animals were sacrificed at 15 and 21 days. No distinct differences were noted between the control and test sites.

EXAMPLE 11

DL-PLA with an inherent viscosity of 0126 dL/g and a molecular weight of about 10,000 was dissolved in NMP to give a 50% by weight polymer solution. SaCl was added to the polymer solution to give a 2.4% by weight dispersion. This material was loaded into a 1-cc disposable syringe fitted with a 23-gauge blunted-end syringe needle, and the material was inserted into the periodontal pocket of a greyhound dog. The material flowed easily out of the narrow syringe tip. The polymer precipitated or coagulated into a film or solid mass when it contacted the saliva and fluid within the pocket. The dog was observed over a time of 2 weeks during which the mass of material remained within the pocket, adhering to tissue surrounding the pocket, and slowly changing color from a light orange to a pale white. The crevicular fluid from the pocket containing the implant was sampled during this 2-week period using Periostrips which are small strips of paper that are placed at the entrance to the periodontal pocket to wick up small quantities of the crevicular fluid within the pocket. The volume of fluid collected is determined using a Periotron which measures the changes in conductance of the paper strip. The Periotron is calibrated before use with a known volume of serum. The paper strip containing the collected fluid is then extracted with a solution of 0.5% by volume of hydrochloric acid in methanol and injected into a liquid chromatograph where the quantity of drug is determined by reference to a known concentration of the same compound. The quantity of SaCl extracted from the paper strip is divided by the quantity of crevicular fluid collected to calculate the concentration of drug in the fluid. With this technique, the concentration of SaCl within the crevicular fluid from the periodontal pocket with the polymeric delivery system was determined to be almost constant during the 2 weeks of observation. The SaCl concentration in the crevicular fluid was 63.2 $\mu$g/mL after 3 days, 80.2 $\mu$g/mL after 7 days, 67.8 $\mu$g/mL after 10 days, and 70.5 $\mu$g/mL after 14 days.

EXAMPLE 12

An illustrative method for the synthesis of an acrylate terminated prepolymer is described. To an oven-dried, 500-mL, three-necked, round-bottom flask fitted with an addition funnel, gas inlet adapter, mechanical stirrer assembly, and rubber septum was added, under nitrogen, 100.0 g of difunctional hydroxy-terminated prepolymer and 200 mL of freshly distilled THF (from $CaH_2$). The flask was cooled in an ice bath, and 24 mL of dry triethylamine (0.95 equiv/equiv OH) was added via a syringe. The addition funnel was charged with 15.4 g of acryloyl chloride (0.95 equiv/equiv OH) in 15 mL of THF, and the solution was added dropwise to the stirred reaction mixture over 1 hour. The mixture was stirred overnight and allowed to reach room temperature. The precipitated triethylamine hydrochloride was removed by filtration, and the filtrate was evaporated in vacuo, affording a pale yellow oil, which was the acrylate-terminated prepolymer. The acylations employing $CH_2Cl_2$ as solvent were conducted in a similar manner. However, the reaction times at 0° C. were shortened to 1 hour, whereupon the reaction mixtures were allowed to reach room temperature over 1 hour. $Et_3N^1HCl$ was filtered out, additional $CH_2Cl_2$ (approximately 800 mL) was added to the filtrate, and the filtrate was extracted several times with 250 mL portions of water. The organic layer was dried over $MgSO_4$/$Na_2SO_4$, filtered, and reduced to an oil in vacuo. The bottles of acrylic prepolymers were wrapped in foil and stored in a refrigerator to safeguard against premature crosslinking.

TABLE 1

SUMMARY OF DIOL PREPOLYMERS SYNTHESIZED

| | Mole ratio of monomers to initiator (ethylene glycol = 1.0) | | Catalyst ($SnCl_2$), | Theoretical | Hydroxyl No., meq OH (56.1)/g | | Gardiner Holdt viscosity, approx. Stokes |
|---|---|---|---|---|---|---|---|
| Sample no. | DL-lactide | ϵ-caprolactone | wt % | $M_n$, daltons | Observed | Theoretical | (T = 22.2° C.) |
| C964-114-1 | 2.4 | 5.0 | 0.03 | 993 | 100 | 113 | 28.0 |
| C964-124-1 | 6.1 | 32.8 | 0.05 | 5036 | 19.7 | 22.3 | Solid |
| C964-128-1 | 2.5 | 5.0 | 0.03 | 993 | 103 | 113 | 28.2 |
| C964-136-1 | 8.0 | 8.0 | 0.03 | 2128 | 48 (est.) | 52.7 | 1375 |

TABLE 2

SUMMARY OF ACRYLIC ESTER TERMINATED PREPOLYMERS SYNTHESIZED

| | Diol precursor | Estimated concentration of acrylic groups, | Reaction conditions | | | |
|---|---|---|---|---|---|---|
| Sample no. | sample no. | meq/g | Temp, ° C. | Time, h | Solvent | Comments |
| C964-118-1 | C964-114-1 | 1.78 | O-RT | 17 | THF | No problems, stable. |
| C964-125-1 | C964-114-1 | 1.78 | O-RT | 17 | THF | Gelled. Overnight exposure to $Et_3N.HCl$ at RT. |
| C964-132-1 | C964-128-1 | 1.84 | 0 | 2 | THF | 100 ppm MEHQ added before workup. |
| C964-137-1 | C964-128-1 | 1.84 | 0 | 2 | $Et_2O$ | Difficult workup. Low yield. |
| C964-139-1 | C964-136-1 | 0.81 | 0 | 2 | THF | Gelled. Overnight exposure to residual $Et_3N.HCl$ in refrigerator. |
| C964-144-1 | C964-136-1 | 0.81 | 0 | 1 | $CH_2Cl_2$ | No problems, stable. |
| C964-146-1 | C964-124-1 | 0.33 | 0 | 1 | $CH_2Cl_2$ | No problems, stable. |

TABLE 3

SUMMARY OF CURING STUDIES

| | Acrylic prepolymer | Benzoyl peroxide | Other additives, | Curing conditions | | Initial Shore A | |
|---|---|---|---|---|---|---|---|
| Sample no. | sample no. | wt % | wt % | Temp, ° C. | Time, h | hardness | Comments |
| C964-120-1 | C964-118-1 | 2.0 | none | 82 | 16 | ND[a] | Rubbery, breaks when bent 180°, weak. |
| C964-120-2 | C964-118-1 | 1.0 | none | 82 | 16 | 83 | Less brittle than C964-120-1. |
| C964-121-1 | C964-118-1 | 2.0 | none | 82 | 16 | 77 | Rubbery, breaks when bent 180°, weak. |
| C964-121-2 | C964-118-1 | 1.0 | none | 82 | 16 | 80 | Slightly stronger than C964-121-1. |
| C964-121-3 | C964-118-1 | 0.5 | none | 82 | 16 | 78 | Slightly more elastic than C964-121-2. |
| C964-121-4 | C964-118-1 | 0.1 | none | 82 | 16 | 69 | Same as C964-121-3. |
| C964-122-1 | C964-118-1 | 1.0 | TMPTETA[b] 46 | 82 | 2.5 | 94 | Less rubbery than C964-120 and C964-121, brittle. |
| C964-122-2 | C964-118-1 | 0.5 | TMPTETA 46 | 82 | 2.5 | 91 | Same as C964-122-1, more flexible. |
| C964-122-3 | C964-118-1 | 1.0 | TMPTETA 175 | 82 | 2.5 | 95 | Not rubbert at all, brittle, weak. |
| C964-122-4 | C964-118-1 | 0.5 | TMPTETA 175 | 82 | 2.5 | 93 | Similar to C964-122-3. |
| C964-123-1 | C964-118-1 | 0.1 | TMPTETA 46 | 82 | 2.5 | 89 | Rubbery, stronger than C964-120 and C964-121, not flexible. |
| C964-123-2 | C964-118-1 | 0.25 | TMPTETA 46 | 82 | 2.5 | 83 | About the same as C964-123-1, may be more brittle. |
| C964-123-3 | C964-132-1 | 0.1 | TMPTETA 175 | 82 | 2.5 | 92 | Not rubbery, strong, brittle. |
| C964-134-1 | C964-132-1 | 0.05 (AIBN)[c] | none | 60[d] | 17 | Liquid | No cure. |
| C964-134-2 | C964-132-1 | 0.10 (AIBN) | none | 60[d] | 17 | Liquid | No cure. |
| C964-134-3 | C964-132-1 | 0.25 (AIBN) | none | 60[d] | 17 | Liquid | No cure. |

TABLE 3-continued

SUMMARY OF CURING STUDIES

| Sample no. | Acrylic prepolymer sample no. | Benzoyl peroxide wt % | Other additives, wt % | Curing conditions Temp, ° C. | Curing conditions Time, h | Initial Shore A hardness | Comments |
|---|---|---|---|---|---|---|---|
| C964-134-4 | C964-132-1 | 0.50 (AIBN) | none | 60[d] | 17 | Liquid | No cure. |
| C964-134-5 | C964-132-1 | 1.00 (AIBN) | none | 60[d] | 17 | Liquid | Slightly thickened. |
| C964-135-1 | C964-132-1 | 0.05 | none | 80[d] | 17 | Liquid | No cure. |
| C964-135-2 | C964-132-1 | 0.10 | none | 80[d] | 17 | Liquid | No cure. |
| C964-135-3 | C964-132-1 | 0.25 | none | 80[d] | 17 | Liquid | No cure. |
| C964-135-4 | C964-132-1 | 0.50 | none | 80[d] | 17 | Liquid | No cure. |
| C964-135-5 | C964-132-1 | 1.00 | none | 80[d] | 17 | Liquid | Slightly thickened. |
| C964-135-6 | C964-128-1[e] | 0.05 | none | 80[d] | 17 | Liquid | No cure. |
| C964-135-7 | C964-128-1[e] | 0.10 | none | 80[d] | 17 | Liquid | No cure. |
| C964-135-8 | C964-128-1[e] | 0.25 | none | 80[d] | 17 | Liquid | No cure. |
| C964-135-9 | C964-128-1[e] | 0.50 | none | 80[d] | 17 | Liquid | No cure. |
| C964-135-10 | C964-128-1[e] | 1.00 | none | 80[d] | 17 | Liquid | No cure. |
| C964-135-11 | C964-124-1[e] | 0.05 | none | 80[d] | 17 | ND | No cure. |
| C964-135-12 | C964-124-1[e] | 0.10 | none | 80[d] | 17 | ND | No cure. |
| C964-135-13 | C964-124-1[e] | 0.25 | none | 80[d] | 17 | ND | No cure. |
| C964-135-14 | C964-124-1[e] | 0.50 | none | 80[d] | 17 | ND | No cure. |
| C964-135-15 | C964-124-1[e] | 1.00 | none | 80[d] | 17 | ND | No cure. |
| C964-141-1 | C964-137-1 | 0.10 | none | 80 | 1 | 66 | Flexible elastomer. |
| C964-141-2 | C964-137-1 | 0.25 | none | 80 | 1 | 71 | Flexible elastomer. |
| C964-141-3 | C964-137-1 | 0.50 | none | 80 | 1 | 72 | Flexible elastomer. |
| C964-141-4 | C964-137-1 | 1.00 | none | 80 | 1 | 72 | Flexible elastomer. |
| C964-141-5 | C964-128-1 | 0.10 | none | 80 | 1 | Liquid | No cure. |
| C964-141-6 | C964-128-1 | 0.25 | none | 80 | 1 | Liquid | No cure. |
| C964-141-7 | C964-128-1 | 0.50 | none | 80 | 1 | Liquid | No cure. |
| C964-141-8 | C964-128-1 | 1.00 | none | 80 | 1 | Liquid | No cure. |
| C964-143-1 | C964-137-1 | 0.25 | Cab-o-Sil PTG, 5.0 | 80 | 1 | 74 | No cure. |
| C964-143-2 | C964-137-1 | 0.25 | Cab-o-Sil PTG, 2.5 | 80 | 1 | 73 | No cure. |
| C964-143-3 | C964-137-1 | 0.25 | L-PLA (IV = 0.8), 5.0 | 80 | 1 | 75 | No cure. |
| C964-143-4 | C964-137-1 | 0.25 | L-PLA (IV = 0.8), 2.5 | 80 | 1 | 78 | No cure. |
| C964-148-1 | C964-144-1 | 0.05 | none | 80 | 17 | Liquid | No cure. |
| C964-148-2 | C964-144-1 | 0.10 | none | 80 | 17 | Liquid | No cure. |
| C964-148-3 | C964-144-1 | 0.25 | none | 80 | 2 | 66 | C964-148-4 and C964-148-6 were about the same in toughness, and both were better than C964-148-3 and C964-148-5. |
| C964-148-4 | C964-144-1 | 0.50 | none | 80 | 2 | 68 | C964-148-4 and C964-148-6 were about the same in toughness, and both were better than C964-148-3 and C964-148-5. |
| C964-148-5 | C964-144-1 | 1.00 | none | 80 | 2 | 67 | C964-148-4 and C964-148-4 were about the same in toughness, and both were better than C964-148-3 and C964-148-5. |
| C964-148-6 | C964-144-1 | 2.00 | none | 80 | 2 | 69 | C964-148-4 and C964-148-4 were about the same in toughness, and both were better than C964-148-3 and C-964-148-5. |
| C964-149-1 | C964-144-1 | 0.15 | none | 80 | 2 | 64 | |
| C964-149-2 | C964-144-1 | 0.20 | none | 80 | 2 | 64 | |
| C964-149-3 | C964-144-1 | 0.25 | none | 80 | 2 | 66 | |
| C964-149-4 | C964-144-1 | 0.15 | Cab-o-Sil N70-TS 5.0 | 80 | 2 | ND | Samples too porous, did not have any flat area for hardness measurement. |
| C964-149-5 | C964-144-1 | 0.20 | Cab-o-Sil N70-TS 5.0 | 80 | 2 | ND | Samples too porous, did not have any flat area for hardness measurement. |
| C964-149-6 | C964-144-1 | 0.25 | Cab-o-Sil N70-TS 5.0 | 80 | 2 | ND | Samples too porous, did not have any flat area for hardness measurement. |
| C964-150-1 | C964-146-1 | 0.05 | none | 80 | 17 | ND | Only partially cured. |
| C964-150-2 | C964-146-1 | 0.10 | none | 80 | 2 | 72 | Elastic, flexible, moderately strong. |
| C964-150-3 | C964-146-1 | 0.25 | none | 80 | 2 | 57 | Elastic, flexible, moderately strong. |
| C964-150-4 | C964-146-1 | 0.50 | none | 80 | 2 | 56 | Elastic, flexible, moderately strong. |
| C964-150-5 | C964-146-1 | 1.00 | none | 80 | 2 | 50 | Elastic, flexible, moderately strong. |
| C964-150-6 | C964-146-1 | 2.00 | none | 80 | 2 | 51 | Elastic, flexible, moderately strong. |

[a]Result not determined.
[b]TMPTETA = trimethylolpropane triethoxy triacrylate.
[c]AIBN = azobisisobutyronitrile.
[d]Cured in air at atmospheric pressure.
[e]Diol prepolymer used.

What is claimed is:

1. A method of forming a solid, biodegradable implant in-situ in a body, comprising:

(a) dissolving a *solid,* water-insoluble, biodegradable, *linear* thermoplastic polymer in a biocompatible, water-soluble organic solvent to form a flowable composition; the organic solvent being capable of dissolving the thermoplastic polymer and being capable of dissipating or diffusing into a body fluid upon placement within a body; and (b) placing the composition into an implant site within the body; and (c) allowing the organic solvent to dissipate or diffuse into body fluid, and the thermoplastic polymer to coagulate or solidify to produce the biodegradable solid implant, wherein the proportion of polymer in solvent and the polymer molecular weight are effective to provide said dissipating or diffusing function and said coagulating or solidifying function.

2. The method of claim 1, wherein the *solid, linear* thermoplastic polymer is selected from the group consisting of polylactides, polyglycolides, polycaprolactones, polydioxanones, polycarbonates, polyhydroxybutyrates, polyalkylene oxalates, polyanhydrides, polyamides, polyesteramides, [polyacetates] *polyacetals*, polyketals, polyorthocarbonates, polyphosphazenes, polyhydroxyvalerates, polyalkylene succinates, poly(amino acids), polyorthoesters, and copolymers, terpolymers, or combinations and mixtures thereof, each named thermoplastic polymer, copolymer, terpolymer, combination or mixture being biodegradable.

3. The method of claim 1, wherein the *solid, linear thermoplastic* polymer is selected from the group consisting of polylactides, polyglycolides, polycaprolactones, and copolymers thereof.

4. The method of claim 1, wherein the organic solvent is selected from the group consisting of N-methyl-2-pyrrolidone, 2-pyrrolidone, acetone, methyl acetate, ethyl acetate, methyl ethyl ketone, dimethylformamide, dimethyl sulfoxide, tetrahydrofuran, caprolactam, decylmethylsulfoxide, oleic acid, and 1-dodecylazacycloheptan-2-one, and combinations and mixtures thereof.

5. The method of claim 1, further comprising combining a biologically-active agent with the *solid, linear* thermoplastic polymer and organic solvent.

6. A pharmaceutical composition for forming a solid biodegradable implant in situ within a body, comprising:

an effective amount of a *solid,* water-insoluble, biodegradable, *linear* thermoplastic polymer dissolved in an effective amount of a biocompatible, water-soluble organic solvent, wherein the solvent is capable of dissolving the thermoplastic polymer and is capable of dissipating or diffusing into a body fluid and the polymer is capable of coagulating or solidifying upon contact with body fluid; and wherein the pharmaceutical composition has a flowable consistency and the molecular weight of the polymer, the amounts of the polymer and the solvent in the pharmaceutical composition are effective to form the solid implant in situ when the pharmaceutical composition contacts body fluid.

7. The pharmaceutical composition of claim 6, wherein the *solid, linear* thermoplastic polymer is selected from the group consisting of:

polylactides, polyglycolides, polycaprolactones, polydioxanones, polycarbonates, polyhydroxybutyrates, polyalkylene oxalates, polyanhydrides, polyamides, polyesteramides, [polyacetates] *polyacetals*, polyketals, polyorthocarbonates, polyphosphazenes, polyhydroxyvalerates., polyalkylene succinates, poly(amino acids), polyorthoesters, and copolymers, terpolymers, or combinations and mixtures thereof each named thermoplastic polymer, copolymer, terpolymer, combination and mixture being biodegradable.

8. The pharmaceutical composition of claim 6, wherein the *solid, linear* thermoplastic polymer is selected from the group consisting of:

polylactides, polyglycolides, polycaprolactones, and copolymers thereof.

9. The pharmaceutical composition of claim 6, wherein the organic solvent is selected from the group consisting of:

N-methyl-2-pyrrolidone, 2-pyrrolidone, acetone, methyl acetate, ethyl acetate, methyl ethyl ketone, dimethylformamide, dimethyl sulfoxide, tetrahydrofuran, caprolactam, decylmethylsulfoxide, oleic acid and 1-dodecylazacycloheptan-2-one, and combinations and mixtures thereof.

10. The pharmaceutical composition of claim 6, further comprising a biologically-active agent combined with the *solid, linear* thermoplastic polymer and organic solvent.

11. The pharmaceutical composition of claim 10, wherein the biologically-active agent is an antibiotic, antimicrobial, peptide drug, protein drug, or a combination thereof.

12. The pharmaceutical composition of claim 10, wherein the biologically-active agent is a tetracycline.

13. The pharmaceutical composition of claim 10, wherein the composition is a homogenous solution, a suspension, or a dispersion.

14. A method of delivering a biologically-active agent to [an animal] *a living body* comprising:

administering a pharmaceutical composition according to claim 10 to the [animal] *living body*, wherein the pharmaceutical composition forms a solid implant and the biologically-active agent is released from the implant into the [animal] *living body*.

*15. An in situ formed biodegradable implant comprising a mixture of a water-insoluble, biodegradable, solid, linear thermoplastic polymer, a biologically active agent and a water-soluble, biocompatible organic solvent, wherein the implant is surrounded by a body tissue, at least some of the polymer is solidified and the remainder of the polymer is in solution with the solvent.*

*16. An implant according to claim 15 wherein the organic solvent has a water solubility, a biocompatibility and a thermoplastic polymer dissolubility exemplified by a compound selected from the group consisting of N-methyl pyrrolidone, 2-pyrrolidone, ethanol, propylene glycol, acetone, methyl acetate, ethyl acetate, methyl ethyl ketone, dimethylformamide, dimethyl sulfoxide, tetrahydrofuran, caprolactam, decylmethyl sulfoxide, oleic acid and 1-dodecylazacycloheptan-2-one.*

*17. An implant according to claim 16 wherein the compound is N-methyl pyrrolidone or dimethyl sulfoxide.*

*18. An implant according to claim 16 wherein the compound is ethyl acetate or oleic acid of 1-dodecylazacycloheptan-2-one.*

*19. An implant according to claim 15 wherein essentially all of the solid, linear thermoplastic polymer is solidified.*

*20. An implant according to claim 19, wherein at least some organic solvent is present in the implant.*

*21. An implant according to claim 19 wherein essentially no organic solvent is present in the implant.*

*22. An implant according to claim 15 wherein the biodegradable, solid, linear thermoplastic polymer is selected from the group consisting of polylactides, polyglycolides, polycaprolactones, polydioxanones, polycarbonates, polyhydroxybutyrates, polyalkyleneoxalates, polyanhydrides, polyamides, polyesteramides, polyacetals, polyketals, polyorthocarbonates, polyphosphazenes, polyhydroxyvalerates, polyalkylenesuccinates, poly(amino acids), polyorthoesters, and copolymers, terpolymers, combinations and mixtures thereof.*

*23. An implant according to claim 22 wherein the linear, solid, thermoplastic polymer is a homopolymer or copolymer of lactide, glycolide, caprolactone or a combination thereof.*

*24. An implant according to claim 15 that is elastomeric.*

*25. An implant according to claim 15 that has a rigidity like that of hard tissue.*

*26. An implant according to claim 15 that is a coagulate.*

*27. An implant according to claim 15 that is a solid.*

*28. An implant according to claim 15 wherein the biologically active agent is an antibiotic, antimicrobial, peptide drug, protein drug, or a combination thereof.*

*29. And implant according to claim 15 wherein the biologically active agent is a peptide drug.*

*30. An implant according to claim 26 that has fully coagulated.*

*31. An implant according to claim 27 that has fully solidified.*

*32. An implant according to claim 15 wherein essentially all of the solid, linear, thermoplastic polymer is a solid and is elastomeric.*

*33. An implant according to claim 15 wherein essentially all of the solid, linear, thermoplastic polymer is a solid and is usable with hard tissue.*

*34. An in situ formed biodegradable implant comprising a mixture of a water insoluble, biodegradable, solid, linear thermoplastic polymer, and a water-soluble, biocompatible organic solvent, wherein the implant is surrounded by a body tissue, at least some of the polymer is solidified, and the remainder of the polymer is in solution with the solvent.*

*35. An in situ formed biodegradable implant comprising a mixture of a water insoluble, biodegradable, solid, linear thermoplastic polymer, and a biologically active agent, wherein the implant is surrounded by a body tissue and the polymer is a solid.*

*36. An in situ formed biodegradable implant comprising a mixture of a water insoluble, biodegradable, solid, linear thermoplastic polymer, and a biologically active agent, wherein the implant is surrounded by a body tissue and the polymer is a solid.*

* * * * *

UNITED STATES PATENT AND TRADEMARK OFFICE

CERTIFICATE OF CORRECTION

PATENT NO. : RE 37,950 E 
DATED : December 31, 2002
INVENTOR(S) : Richard L. Dunn Ph.D. et al.

It is certified that error appears in the above-identified patent and that said Letters Patent is hereby corrected as shown below:

Title page, Item [54] and Column 1, line 1,
Delete "BIOGRADABLE" and insert -- BIODEGRADABLE -- therefor.

Title page,
Item [56], OTHER PUBLICATIONS, delete "Materisl" and insert -- Materials -- therefor.
U.S. PATENT DOCUMENTS, delete "434/426" and insert -- 424/426 -- therefor.

Column 2,
Line 20, insert -- as -- after "such".

Column 3,
Line 19, delete "a" before "dispersion".
Line 38, delete "of" after "DL-lactide" and insert -- or -- therefor.

Column 6,
Line 66, delete second instance of "antiallergenics, steroidal anti-inflammatory agents,".

Column 8,
Line 12, delete "concentration" and insert -- concentrations --, therefor.
Line 32, delete "Were" and insert -- were -- therefor.

Column 9,
Line 25, delete "sytringe" and insert -- syringe -- therefor.
Line 26, delete "mxiture" and insert -- mixture -- therefor.

Column 10,
Line 60, delete "loading" and insert -- loadings -- therefor.

Column 11,
Line 17, delete "of" after "oligomer" and insert -- or -- therefor.
Line 35, detete "to" after "weight solution" and insert -- of -- therefor.
Line 65, delete "at" after "chloride" and insert -- as -- therefor.

Columns 13-14, Table 3,
Line 11, under "Comments", delete "," after "C964-121" and insert -- ; -- therefor.
Line 18, under "Comments", delete "C964-132-1" and insert -- C964-118-1 --, therefor.
Line 20, under "Comments", delete "," after "rubbery" and insert -- ; -- therefor.

UNITED STATES PATENT AND TRADEMARK OFFICE

CERTIFICATE OF CORRECTION

PATENT NO. : RE 37,950 E
DATED : December 31, 2002
INVENTOR(S) : Richard L. Dunn Ph.D. et al.

It is certified that error appears in the above-identified patent and that said Letters Patent is hereby corrected as shown below:

Column 17,
Line 27, delete "," after "terpolymers"
Line 30, delete "or" after "combination" and insert -- and --, therefor.
Lines 48 and 61, delete "in situ" and insert -- in-situ -- therefor.

Column 18,
Line 4, delete "." after "polyhydroxyvalerates".
Line 7, insert -- , -- after "thereof".
Line 41, delete "in situ" and insert -- in-situ -- therefor.
Line 60, delete "of" and insert -- or -- therefor.
Line 64, delete "," after "19".

Column 19,
Line 24, delete "And" and insert -- An -- therefor.

Column 20,
Lines 10, 16 and 21, delete "in situ" and insert -- in-situ -- therefor.

Signed and Sealed this

Eighth Day of July, 2003

JAMES E. ROGAN
*Director of the United States Patent and Trademark Office*